United States Patent [19]
Folta

[11] Patent Number: 5,644,395
[45] Date of Patent: Jul. 1, 1997

[54] MINIATURIZED FLOW INJECTION ANALYSIS SYSTEM

[75] Inventor: James A. Folta, Livermore, Calif.

[73] Assignee: Regents of the University of California, Oakland, Calif.

[21] Appl. No.: 502,795

[22] Filed: Jul. 14, 1995

[51] Int. Cl.[6] .............................. G01N 1/10; G01N 21/01
[52] U.S. Cl. ............................................ 356/246; 356/244
[58] Field of Search ............................ 356/246, 244; 73/23.22, 23.35, 23.41, 23.42, 864.81, 864.83, 863.71; 148/187

[56] References Cited

U.S. PATENT DOCUMENTS 3,895,976  7/1975  Dumas ............................ 148/187
5,487,313  1/1996  Johnson ........................ 73/863.71

Primary Examiner—Frank Font
Assistant Examiner—Michael P. Stafira
Attorney, Agent, or Firm—Henry P. Sartorio; L. E. Carnahan

[57] ABSTRACT

A chemical analysis technique known as flow injection analysis, wherein small quantities of chemical reagents and sample are intermixed and reacted within a capillary flow system and the reaction products are detected optically, electrochemically, or by other means. A highly miniaturized version of a flow injection analysis system has been fabricated utilizing microfabrication techniques common to the microelectronics industry. The microflow system uses flow capillaries formed by etching microchannels in a silicon or glass wafer followed by bonding to another wafer, commercially available microvalves bonded directly to the microflow channels, and an optical absorption detector cell formed near the capillary outlet, with light being both delivered and collected with fiber optics. The microflow system is designed mainly for analysis of liquids and currently measures 38×25×3 mm, but can be designed for gas analysis and be substantially smaller in construction.

17 Claims, 5 Drawing Sheets

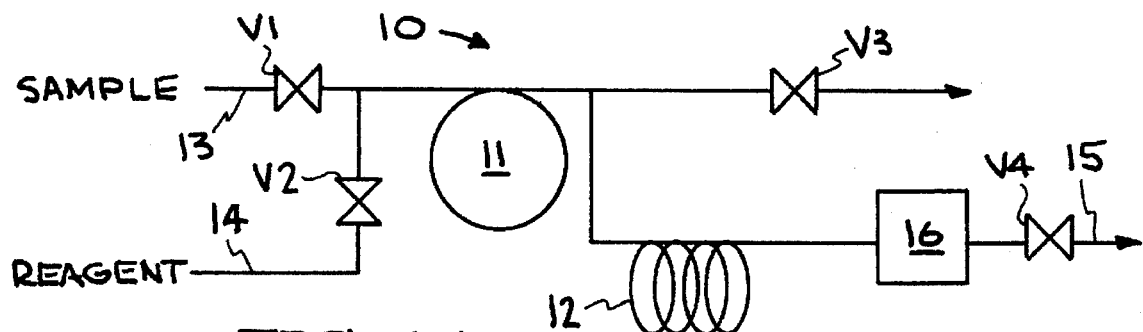
FIG. 1A
```
            ANALYSIS  SEQUENCE
    STEP              V1   V2   V3   V4
1  REAGENT FILL       C    O    C    O
2  SAMPLE LOAD        O    C    O    C
3  INJECT + ANALYZE   C    O    C    O
    O = OPEN       C = CLOSED
```
FIG. 1B
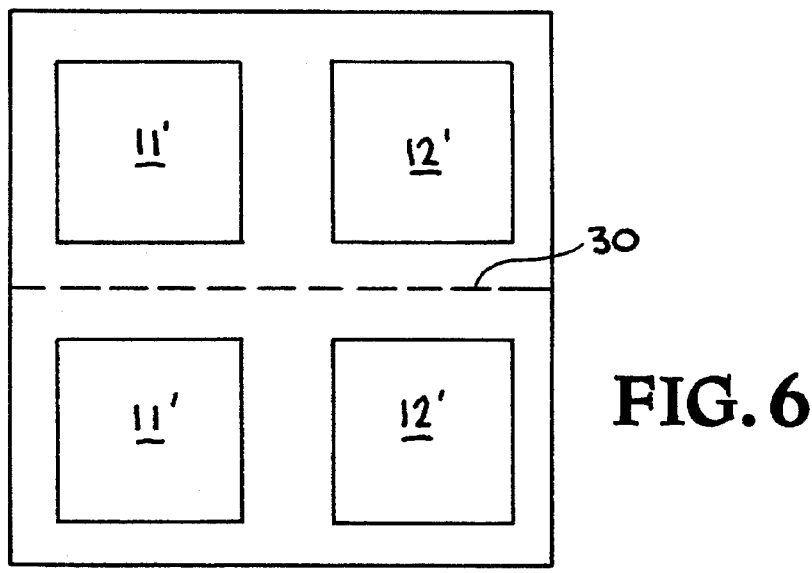
FIG. 6

MINIATURIZED FLOW INJECTION ANALYSIS SYSTEM

The United States Government has rights in this invention pursuant to Contract No. W-7405-ENG48 between the United States Department of Energy and the University of California for the operation of Lawrence Livermore National Laboratory.

BACKGROUND OF THE INVENTION

The present invention relates to chemical analysis techniques, particularly to flow injection analysis systems, and more particularly to a miniaturized flow injection analysis system composed of a microflow system formed between bonded wafers, surface-mounted microvalves connected in the microflow system, and a detection cell.

The general concept of the chemical analysis technique known as flow injection analysis (FIA), involves small quantities of chemical reagents and a sample (liquid, gas, etc.) which are intermixed and reacted within a capillary flow system and the reaction products are detected optically, electrochemically, or by other means. An FIA system can consist of pumps (fluid or vacuum), valves, flow capillaries, flow separators, extractors, absorbers, and/or detectors. FIA systems provide inexpensive analysis of chemicals, foods, engine oil, environmental sensing, biological samples, etc., and thus have wide applications.

Silicon microfabrication technology developed for the semiconductor microelectronics industry is being increasingly applied to other scientific fields such as mechanical engineering, chemistry, biochemistry, and physics. Recent advances in micro-optics, micro-electro-mechanical systems (MEMS), and other microcomponents such as microflow channels, solid state optical and chemical detectors, thin membranes, analog and digital electronics, and recently microvalves, enable the development of revolutionary integrated microanalytical systems in much the same way that integrated circuits revolutionized the microelectronics industry.

One of the most promising new applications of MEMS in terms of performance and potential impact is development of analytical chemical microinstrumentation. The quantities and volumes required for chemical analyses and the forces required in analytical instrumentation are most compatible with the micron-scale of dimensions and forces encountered in MEMS. In addition, miniaturized instrumentation can be developed which will offer some unique advantages for applications involving in-situ analysis of trace quantities of substances. Micro-analytical instruments developed using integrated circuit-like microfabrication technology may have significant advantages in terms of performance, greatly reduced size, weight and costs—especially if wafer level fabrication techniques such as used to build integrated circuits can be adopted to allow automated and batch production of multiple micro-instruments on a wafer.

Four primary advantages exist for flow injection analysis. First the sensing system can be both sensitive and selective because the detector is optimized for sensitivity alone without regard to selectivity while the chemical reagents and flow system are optimized to yield high selectivity toward the contaminant of interest. For example hexavalent chromium has been detected at levels as low as 18 ppb with FIA. This is in contrast to most chemical sensors in which a difficult tradeoff exists between sensitive and selective detection. Second, analysis times are usually just a few minutes; the rapid throughput allows analysis of 2040 samples per hour. Third, the small size of the capillary minimizes the amount of reagents required and the volume of waste generated by the analytical procedure. Fourth, FIA is ideally suited for miniaturization-performance improves with reduced size. FIA is robust in the wide range of operating parameters under which one can achieve successful analyses; this allows the microdevice designer wide latitude in selecting among various trade-offs required during system development. Finally, recent advances in microfabricated valves, capillaries, microelectrodes, and optical sources and detectors allow development of miniature flow injection systems.

While recent efforts have been directed in miniaturization of FIA systems, the development of miniaturized FIA components has been successfully demonstrated, and the present invention provides integration of the components into a working system. The system of this invention comprises three (3) components; namely, a microflow system formed between bonded wafers or substrates, 2) surface-mounted microvalves, and 3) an optical absorption detection cell with fiber optics.

SUMMARY OF THE INVENTION

An object of the present invention is to provide a miniaturized flow injection analysis (FIA) system.

A further object of the invention is to provide an FIA system utilizing a micro flow system formed between bonded substrates.

A further object of the invention is to provide an FIA system using an absorption detection cell in combination with a microflow system.

Another object of the invention is to provide an FIA system utilizing an optical absorption detection cell with fiber optics.

Another object of the present invention is to provide an FIA system using micro-valves in conjunction with a microflow system formed between bonded substrates and an optical absorption detection cell using fiber optics.

Other objects and advantages of the present invention will become apparent from the following description and accompanying drawings. The invention involves a highly miniaturized version of an FIA system using components fabricated by microfabrication techniques common to the microelectronics industry. The system uses microflow channels and capillaries formed by etching microchannels in a substrate or wafer, such as silicon or glass, followed by bonding to another substrate or wafer. Microvalves, available commercially, are bonded directly to the microflow channels. An optical absorption detection cell is formed near the capillary outlet, and light is both delivered and collected with fiber optics. A prototype microflow system has been designed mainly for analysis of liquids and currently measures 38×25×3 mm. The prototype was designed for analysis of heavy metals, particularly chromium and mercury, in ground water and aqueous waste process streams. However, the FIA system of this invention can be designed and/or utilized wherever there is a need for analysis involving small quantities of reagents and sample which are intermixed and reacted within a capillary flow system and the reaction products are detected.

The present invention has a wide variety of applications including environmental sensing, biomedical, clinical, chemical process control, nonproliferation, as well as analysis of chemicals, foods, engine oil, or other consumer products.

BRIEF DESCRIPTION OF THE DRAWINGS

The accompanying drawings, which are incorporated into and form a part of the disclosure, illustrate an embodiment of the invention and, together with the description, serve to explain the principles of the invention.

FIG. 1A is a schematic illustration of an embodiment of a flow diagram of a flow injection analysis (FIA) system.

FIG. 1B is an analysis sequence of the valve activation of the FIG. 1A FIA system.

FIG. 6 illustrates two FIA systems as shown in FIG. 5 fabricated on a single wafer pair.

DETAILED DESCRIPTION OF THE INVENTION

Figure 2:
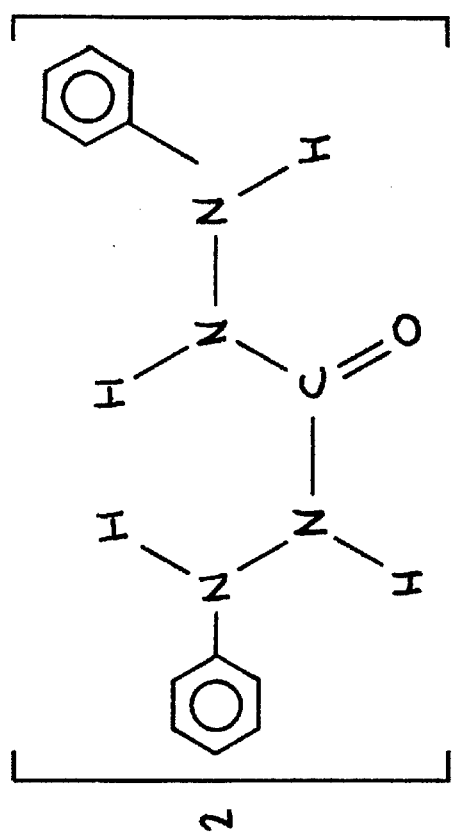
FIG. 2 illustrates a selected FIA test bed chemistry utilized in verifying the invention.
Figure 2:
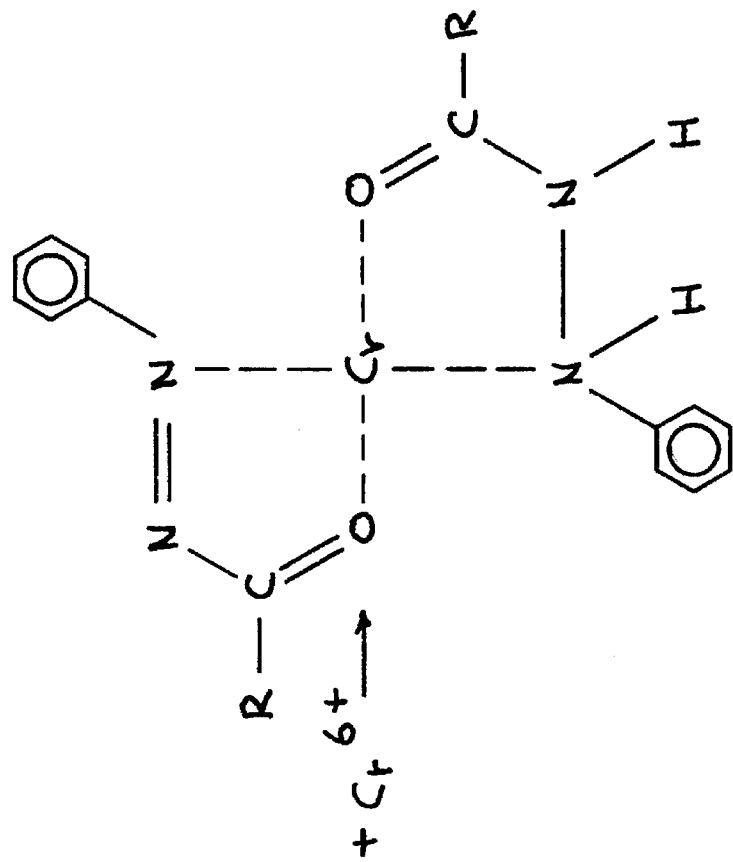

The invention is directed to miniaturized flow injection analysis (FIA) systems in which small quantities of at least one chemical reagent and a sample (generally liquid or gas) are intermixed and reacted within a capillary flow system and the reaction products are detected optically, but can be detected electrochemically or by other means. A prototype highly miniaturized FIA system has been designed, as illustrated in FIGS. 3A,3B-6, for analysis of heavy metals, particularly chromium and mercury, in ground water and aqueous waste process streams.

The highly miniaturized FIA system of this invention involves forming a microflow system by etching microchannels in a substrate, such as silicon or glass, followed by bonding to another substrate to seal the channels from each other. Commercially available microvalves are bonded directly to the microflow system. An optical absorption detection cell is formed near the capillary outlet, and light is both delivered and collected with fiber optics. The internal surfaces of the detection cell are usually highly polished to mirror-like surfaces to provide a light-pipe effect. The high reflectivity provides near total-internal-reflectance which greatly increases the transmission efficiency of the cell. The use of optical fibers to both deliver and collect light allows use of compact light sources (e.g. light-emitting diodes) and detectors (e.g. photodiodes), and allows substitution of different sources and detectors depending on the application. The prototype illustrated in FIGS. 3A, 3B-6 is designed mainly for analysis of liquids and measures 38×25×3 mm, but could be significantly smaller.

The primary benefits of the invention include reduced size and cost, reduced chemical usage and waste generation, ability to analyze minute samples, and decreased analysis time. Reliability may be higher owing to redundancy of microcomponents. Unlike many other microsensors, an FIA can provide both sensitive and selective detection simultaneously.

The miniaturized FIA system of this invention has numerous current and potential uses, such as chemical analysis for environmental sensing, site characterization, and monitoring; chemical analysis for biomedical and clinical applications; chemical analysis for intelligence, non-proliferation, and treaty verification; real time chemical analysis for chemical process control; inexpensive chemical analysis of agricultural chemicals, foods, engine oil, fuel spills, or other consumer products; as well as for space experiments.

Referring now to the drawings, FIG. 1A illustrates the general concept of FIA, wherein small quantities of reagents and water sample are intermixed and reacted within a capillary flow system and the reaction products are detected optically, or detected electrochemically or otherwise. As shown in FIG. 1A, the basic components comprise a flow system generally indicated at 10, which includes a sample loop 11 and a reaction capillary 12, and in which valves V1, V2, V3 and V4 are bonded for controlling the flow of sample 13, reagent 14, and waste product indicated at 15 there through. An optical detector 16 is located at the outlet of the reaction capillary 12.

FIG. 1B sets forth the analysis sequence, and the open (o) or closed (c) position of valves V1–V4 of FIG. 1A during the steps of: 1) reagent fill, 2) sample inject, and 3) analyze. The sample volume is fixed by the volume of the sample loop. For injecting samples into reagent streams, the loop is filled with sample in step 2; in step 3, the sample is injected into the reagent stream and flowed through the capillary. Alternately, a fixed volume of reagent could be injected into a stream of sample. These are referred to as hydrodynamic injections. Other injection methods are also commonly used.

FIG. 2 shows the selected test bed chemistry for detection of chromium in an aqueous solution. Hexavalent chromium, Cr(VI), reacts with 1, 5-diphenylcarbazide to form a purple complex which absorbs strongly at a wavelength of 540 nm. The chromium chemistry was chosen for its simplicity (only a single mixing step is required) and the availability of green light emitting diodes which are small, reliable, inexpensive, and provide the proper wavelength.

Figure 3A:
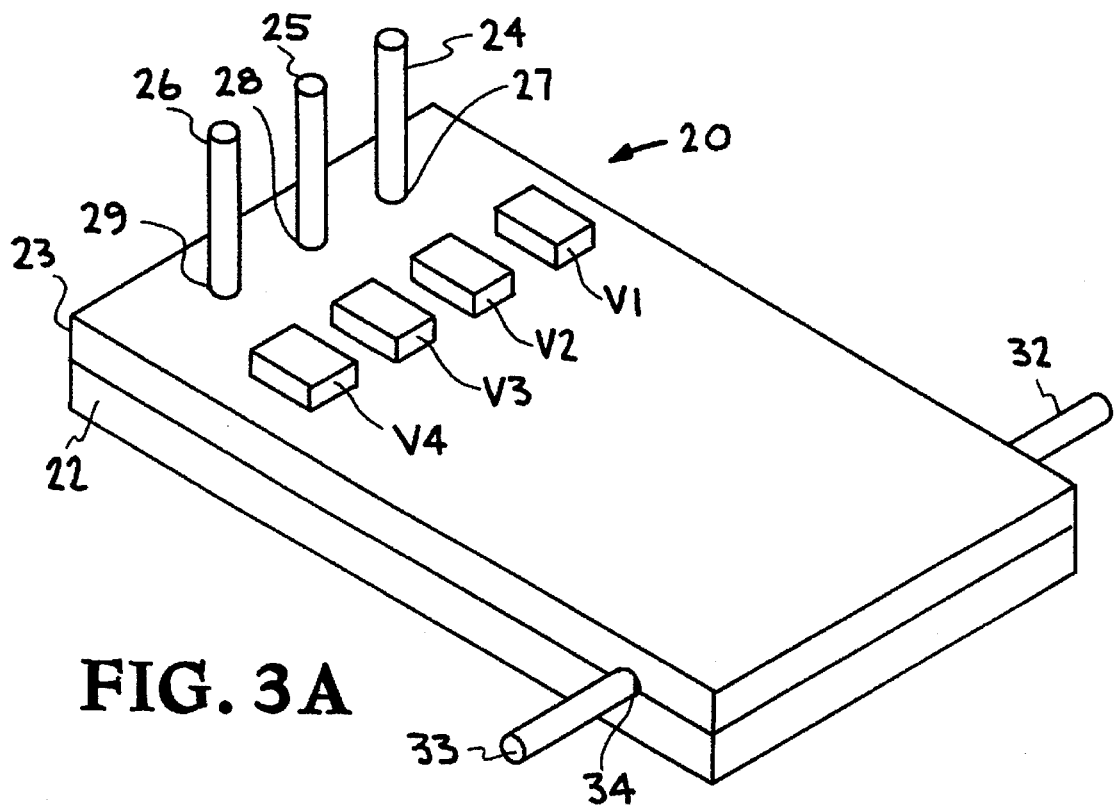
FIGS. 3A and 3B show a conceptual illustration of the miniaturized FIA system of the invention.
Figure 3B:
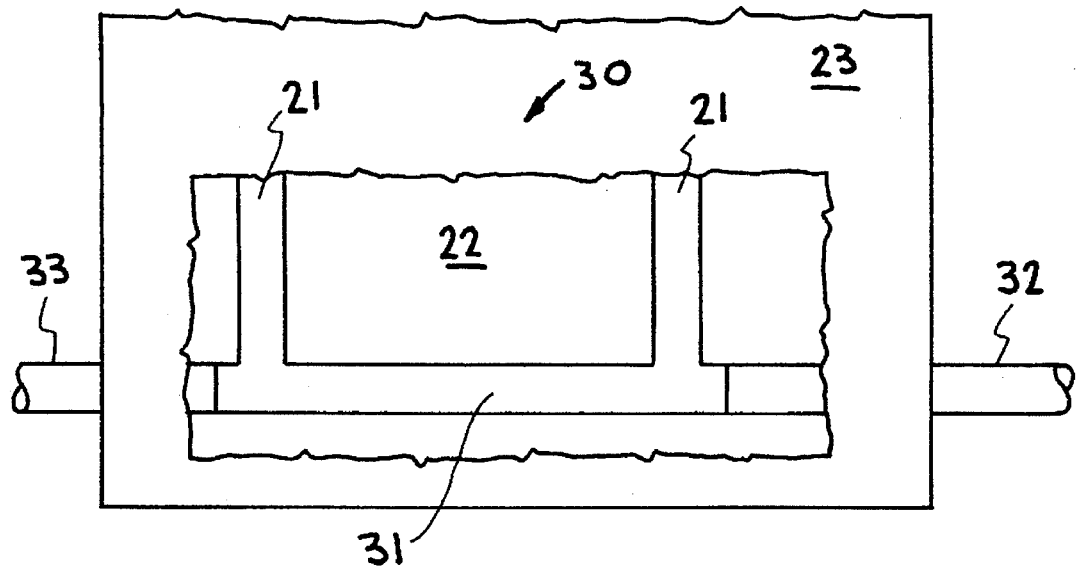

FIGS. 3A–3B conceptually illustrate the miniaturized (38 mm×25 mm×3 mm) prototype FIA sensor which consists of three (3) major components: microvalves, the microflow system, and the optical absorption detection cell. The first component, the microvalves, generally dedicated at 20, comprising valves V1, V2, V3 and V4 of FIG. 1A are commercially produced by Redwood MicroSystems, Inc., Menlo Park, Calif., and are mounted so as to control the microflow system. The second subcomponent, the microflow system, is formed by etching or otherwise forming grooves or flow microchannels 21 (see FIG. 4A) in a substrate 22, such as a Pyrex (glass) wafer having a length of 5 cm and width of 3 cm, followed by wafer-to wafer bonding of a cover plate or layer 23, such as a silicon wafer, to the Pyrex wafer 22. The bonding of wafers 22 and 23 may be carried out by any conventional technique, such as eutectic alloy, anodic Si-to-glass, Si-to-Si fusion bonding, or adhesives. The microchannels 21 have a cross-section or diameter of 1 to 1000 µm. Wafer 22 has a thickness of 200 to 1000 µm and wafer 23 has a thickness of 200 to 1000 µm. While FIG. 3A,3B illustrates the flow microchannels or grooves 21 as being formed in substrate 22, such could be formed in the silicon cover wafer 23, or both. More complicated FIA systems may comprise a stack of multiple wafers all bonded together. A plurality of tubes or lines, composed of a sample inlet 24, a reagent inlet 25 and a vacuum supply to waste outlet 26 extend through and are secured in openings 27, 28 and 29 in silicon cover plate 23 and are in fluid communication with certain of the flow channels 21 (see FIG. 4A). The third component, the optical absorption detection cell is of a flow-through optical absorption type, and is composed of an optical absorption flow cell 30 including a tube or line 31 connected to flow channels 21, and to which is connected a pair of optical fiber assemblies 32 and 33, with fiber assembly 32 being an optical fiber source providing light into cell 30 and fiber assembly 33 being an optical fiber detector taking light out of cell 30. The optical absorption flow cell 30 and the optical fiber assemblies 32 and 33 are conventionally known and utilized optical detection arrangements and details or operation thereof need not be described herein, except for the aforementioned improved features of the light pipe optical absorption detection cell. Use of fiber optics to deliver and collect light provides two advantages: 1) ease of construction, and 2) greater flexibility to exchange light sources and detectors for analysis of other contaminants of interest. As shown in FIG. 3A, the flow cell 30 and optical fiber assemblies 32 and 33 are mounted in and extend 23, b a channel 34 formed (etched) in wafers 22 and 23, but could be formed in either of the wafers. The substrate 22 may be composed of Pyrex, glass, silicon, plastic and ceramic, while the cover wafer 23 may be composed of silicon, Pyrex, glass, plastic, and ceramic.

Figure 4A:
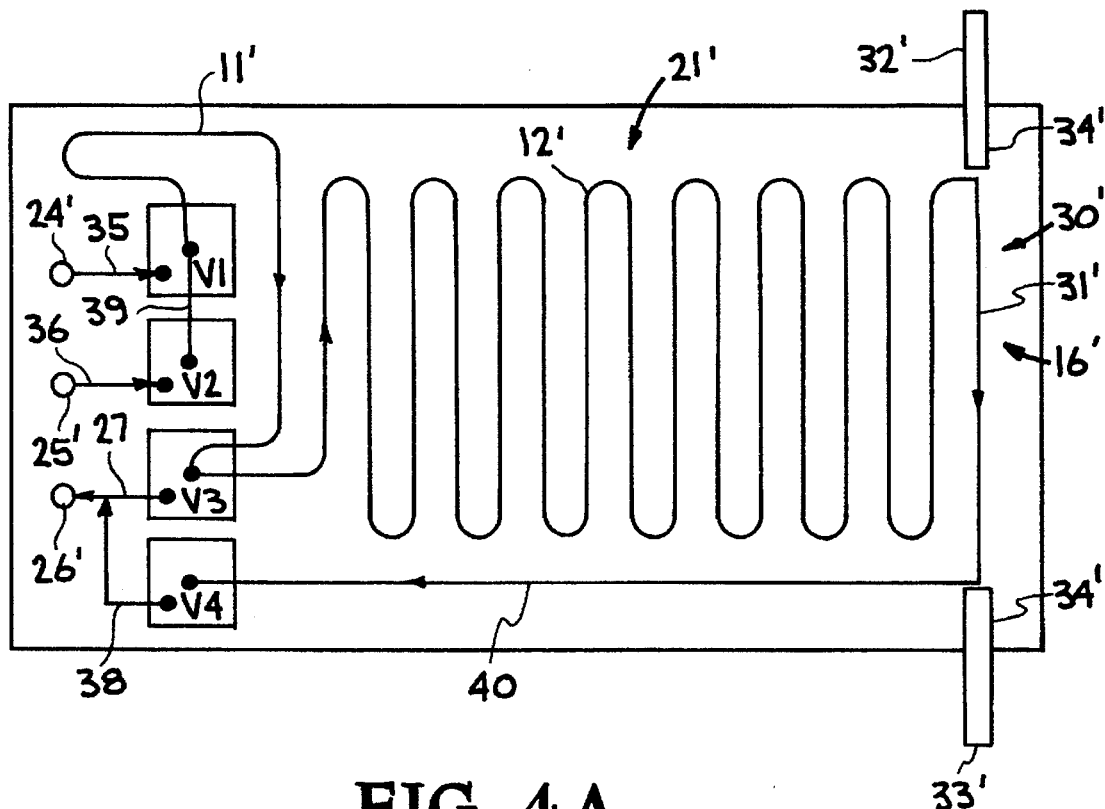
FIG. 4A is a schematic plan view of an embodiment of the FIA microsensor made in accordance with the present invention.
Figure 4B:
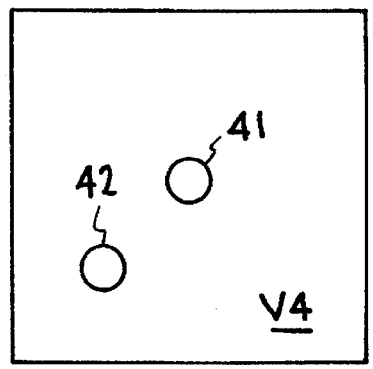
FIG. 4B is an enlarged view of valve V4 of FIG. 4A.

FIGS. 4A–4B show an enlarged simplified plan view of the pattern used to etch the flow channels of the prototype built and tested in accordance with the present invention. Reference numerals for components similar to the FIGS. 1A and 3A embodiment are utilized in FIG. 4A. As illustrated, the FIA comprises a substrate 22, composed of silicon, glass, Pyrex, etc., which can be readily etched or grooved to form flow microchannels generally indicated at 21'. These flow microchannels are configured and formed to produce a sample loop section 11', a mixing and reaction capillary section 12', and an optical detection section 16'. In addition, channels 35, 36, and 37 are formed to interconnect valves V1, V2 and V3 mounted on the surface of cover plate 23, with sample inlet port 24', reagent inlet port 25', and vacuum port 26'. A channel 38 is formed to interconnect valve V4, mounted on cover plate 23, with vacuum port 26'. Valves V1 and V2 are interconnected by a channel 39 with valve V1 being connected to sample loop section 11'. Valve V3 is interconnect intermediate sample loop section 11' and mixing and reaction capillary section 12' and to vacuum port 26'. Valve V4 is connected to the optical detector section 16' via a channel 40 and to vacuum port 26'. Optical detector section 16', as in FIG. 3A,B, includes an optical absorption flow cell 30', and optical fiber assemblies 32' and 33', with components 30', 32' and 33' being located in channel 34' in substrate 22. Microvalves V1, V2, V3 and V4, each are provided with inlet/outlet ports, generally indicated at 41 and 42 in the enlargement of valve V4. In FIG. 4A, flow arrows show the direction of fluid flows through the various components of the FAI system during analysis of a desired sample.

Figure 5:
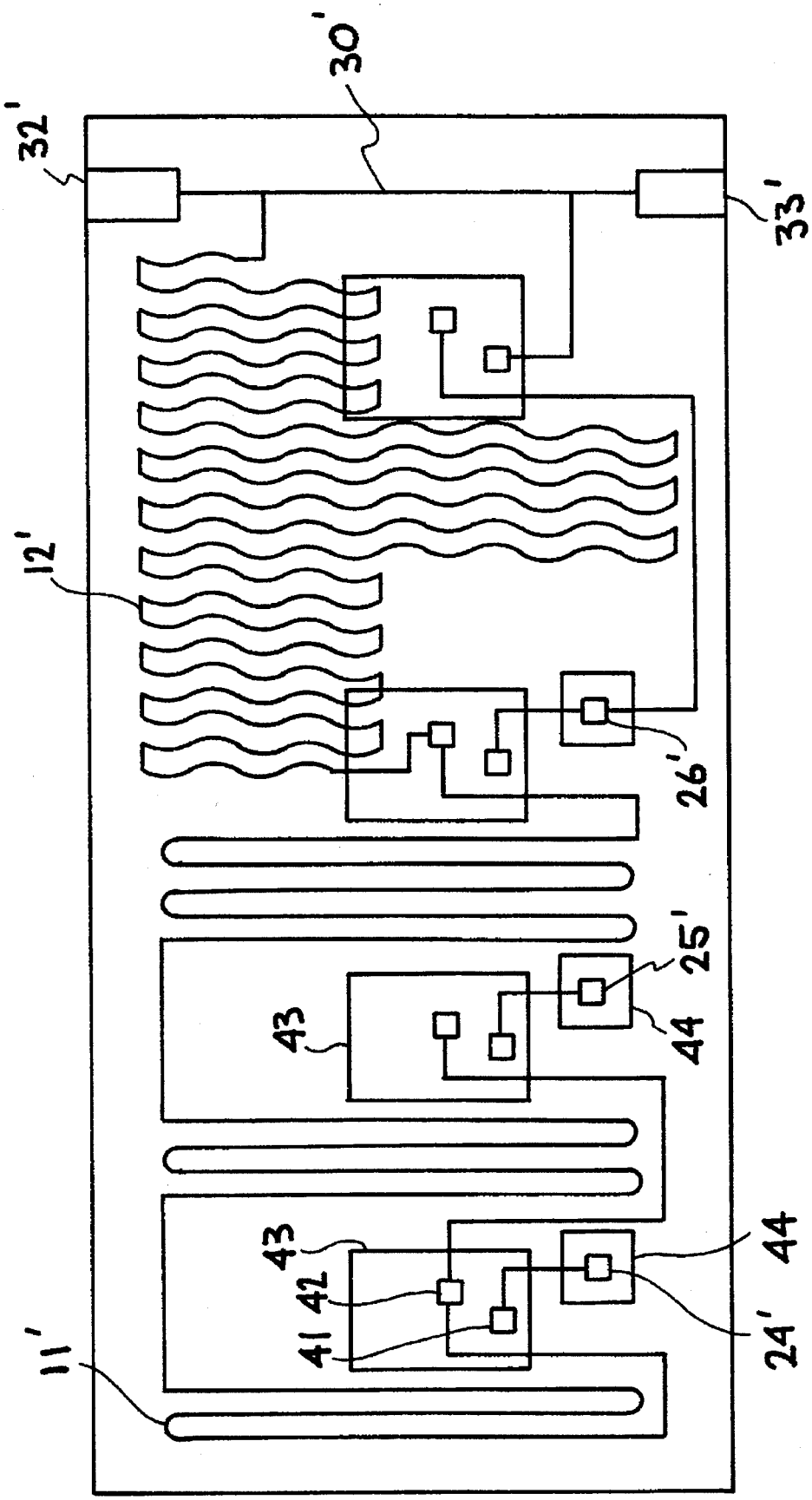
FIG. 5 illustrates the microflow details of the various components of the FIG. 4A FIA system.

FIG. 5 shows the actual lithographic mask patterns, magnified 3.3×, including shallow indented areas 43 and 44 used to align the microvalve inlet 41 and outlet 42 and tubing connectors to the access ports. The various components similar to those in FIG. 4A are given corresponding reference numerals.

FIG. 6 shows the mask design for a pair of FIA systems as shown in FIG. 5 fabricated on a three (3) inch diameter wafer. Separation of the two systems fabricated on the same wafer pair (e.g. sawing) allows final assembly of the FIA systems.

Two versions of the instrument (FIA system) are currently being considered:
1) A portable system for real-time field analysis and on-line monitoring of process or waste streams; and
2) the highly miniaturized version for deployment via cone penetrometers or as a fixed underground monitor of contaminant migration.

In the verification experiments detection of hexavalent chromium was selected as the test bed chemistry because of its relative ease of implementation and more importantly because of the stated need for heavy metal detection in the Department of Energy's Characterization, Monitoring and Sensing Technologies-Integrated Program (CMST-IP). The highly miniaturized version of the FIA sensor of this invention will be packaged to allow deployment by cone penetrometers for measurement of heavy metal contaminants in ground water. In fact, the reason for the selection of vacuum to transport liquids through the FIA sensor was its compatibility with remote deployment techniques. A single low vacuum line can be used to aspirate water samples and reagents into and through the detector. However, the system can also be operated by pressurizing the reagent inlet.

It has thus been shown that the present invention provides a miniaturized flow injection analysis system which has broad applications, and particularly for the analysis of small samples of various materials. The primary benefits of the invention include reduced size and cost, reduced chemical usage and waste generation, ability to analyze minute samples, and decreased analysis time. Unlike many other microsensors, the FIA system can provide both sensitive and selective detection simultaneously.

While particular embodiments, materials, parameters, etc. have been illustrated or described to enable an understanding of the invention, such are not intended to be limiting. Modifications and changes may become apparent to those skilled in the art, and it is intended that the invention be limited only by the scope of the appended claims.

The invention claimed is:

1. A miniaturized flow injection analysis system, comprising:
   a substrate having flow channels formed therein;
   a cover member secured to said substrate to cover said flow channels;
   said flow channels including a sample loop section, a mixing and reaction capillary section, and an absorption section;
   a plurality of microvalves operatively connected to sections of said flow channels;
   at least sample, reagent, and waste ports operatively connected to said microvalves; and
   a detector assembly operatively connected to said absorption section, said detector assembly including an optical absorption flow cell, a fiber optic source, and a fiber optic detector, said fiber optic source and detector being operatively connected to said optical absorption flow cell.

2. The system of claim 1, wherein a first of said microvalves is operatively connected to a sample inlet port, wherein a second of said microvalves is operatively connected to a reagent inlet port, wherein a third of said microvalves is connected intermediate said sample loop section and said mixing and reaction capillary section, and wherein a fourth of said microvalves is operatively connected to a waste outlet port.

3. The system of claim 2, wherein at least one of said microvalves is additionally connected to a vacuum port.

4. The system of claim 3, wherein said third and fourth microvalves are operatively connected to said vacuum port.

5. The system of claim 1, wherein said optical absorption flow cell, and at least portions of said fiber optic source and detector are positioned intermediate said substrate and said cover member.

6. The system of claim 1, additionally including a vacuum port operatively connected to at least said waste port.

7. The system of claim 6, wherein said vacuum port is additionally connected through one of said microvalves intermediate said sample loop section and said mixing and reaction capillary section of said flow channels.

8. In a flow injection analysis system, the improvement comprising miniaturization of the components thereof which are at least partially located intermediate a substrate and a cover member, said components including:

flow microchannels formed in at least one of said substrate and cover member;

said flow microchannels defining a sample loop section, a mixing and reaction capillary section and an absorption flow section; and a plurality of microvalves operatively connected to said flow microchannels;

an optical absorption flow cell operatively connected to an outlet end of said mixing and reaction capillary section of said flow microchannel;

said absorption flow cell being located within said substrate and cover member; and a fiber optics source and a fiber optics detector operatively connected to said optical absorption flow cell.

9. The improved system of claim 8, additionally including a sample inlet port, a reagent inlet port, and a waste outlet port, each of said ports being operatively connected to said flow microchannels via one of said microvalves.

10. The improved system of claim 9, additionally including a vacuum port operatively connected to at least said waste outlet port.

11. The improved system of claim 10, wherein said vacuum port is additionally connected intermediate said sample loop section and said mixing and reaction capillary section of said flow microchannels via one of said microvalves.

12. The improved system of claim 10 wherein said sample inlet port is operatively connected to one end of said sample loop section of said flow microchannels, via a first of said plurality of microvalves;

wherein said reagent inlet port is operatively connected to said sample loop section via a second of said plurality of microvalves;

wherein said waste outlet port is connected to an outlet end of said absorption flow section of said flow microchannels via a third of said plurality of microvalves; and additionally including a vacuum port operatively connected to said waste outlet port and to a fourth of said plurality of microvalves, said fourth of said plurality of microvalves being also connected to said flow microchannels intermediate said sample loop section and said mixing and reaction capillary section.

13. The improved system of claim 8, wherein a tube is connected to each of said sample inlet port, said reagent inlet port, and said waste outlet port and vacuum port.

14. The improved system of claim 9, wherein said plurality of microvalves comprises four microvalves, each having an inlet port and outlet port, a first microvalve having its inlet port connected to said sample inlet port and its outlet port connected to said sample loop section, a second microvalve having its inlet port connected to said reagent inlet port and its outlet connected to said sample loop section;

a third microvalve having its inlet port connected intermediate said sample loop section and said mixing and reaction capillary section and its outlet connected to said waste outlet port, wherein said waste outlet port additionally defines a vacuum port, and a fourth microvalve having its inlet port connected to said absorption flow section and its outlet port connected to said waste outlet port, said vacuum port, and said outlet port of said third microvalve.

15. The improved system of claim 8, wherein said flow microchannels have a cross-section in the range of 1 to 1000 µm.

16. The improved system of claim 8, wherein said substrate is composed of material selected from the group consisting of Pyrex, glass, silicon, plastic, and ceramic; and wherein said cover member is composed of material selected from the group consisting of silicon, Pyrex, glass, plastic, and ceramic.

17. The improved system of claim 16, wherein said substrate is composed of Pyrex, wherein said cover member is composed of silicon, and wherein said substrate and said cover member are bonded together to form at least said flow microchannels therein.

* * * * *